US005736525A

United States Patent [19]

Hovanessian et al.

[11] Patent Number: 5,736,525
[45] Date of Patent: Apr. 7, 1998

[54] COMPLEXES OF POLYADENYLIC ACID WITH POLYURIDYLIC ACID

[75] Inventors: Ara G. Hovanessian, Bourg la Reine; Evelyne Deschamps de Paillette, Paris, both of France

[73] Assignee: Societe de Conseils de Recherches et d'Applications Scientifiques (S.C.R.A.S.), France

[21] Appl. No.: 816,643

[22] Filed: Mar. 13, 1997

Related U.S. Application Data

[62] Division of Ser. No. 582,658, Jan. 4, 1996, which is a continuation of Ser. No. 437,219, May 8, 1995, abandoned, which is a continuation of Ser. No. 218,850, Mar. 28, 1994, abandoned, which is a continuation of Ser. No. 99,048, Jul. 28, 1993, abandoned, which is a continuation of Ser. No. 866,435, Apr. 10, 1992, abandoned.

[30] Foreign Application Priority Data

Apr. 16, 1991 [GB] United Kingdom ............. 91-08085

[51] Int. Cl.[6] ................................................. A61K 48/00
[52] U.S. Cl. ........................................................ 514/44
[58] Field of Search ................................................ 514/44

[56] References Cited

U.S. PATENT DOCUMENTS 5,063,209 11/1991 Carter ............................................ 514/44

OTHER PUBLICATIONS

Cell Biology International Reports, Vo. 14, Dec. 1980, No. 12.
Journal of Immunology, vol. 117, pp. 423–427 Aug. 1976.
Clinical Aspects of Interferons, pp. 319–331 1988.

*Primary Examiner*—John L. LeGuyader
*Attorney, Agent, or Firm*—Bierman, Muserlian and Lucas LLP

[57] ABSTRACT

The invention relates to a method of treating and a therapeutical composition for the treatment of Acquired Immuno Deficiency Syndrome (AIDS) and related infections. The composition comprises from 1 to 100% of a complex of Poly(A).Poly(U), preferably associated with other anti-AIDS coagents which act on the HIV virus according to a different mechanism from that of the complex of Poly(A) .Poly(U). The composition is suitably administered in 100 to 4000 mg doses and at 3 to 5 day intervals.

13 Claims, 1 Drawing Sheet

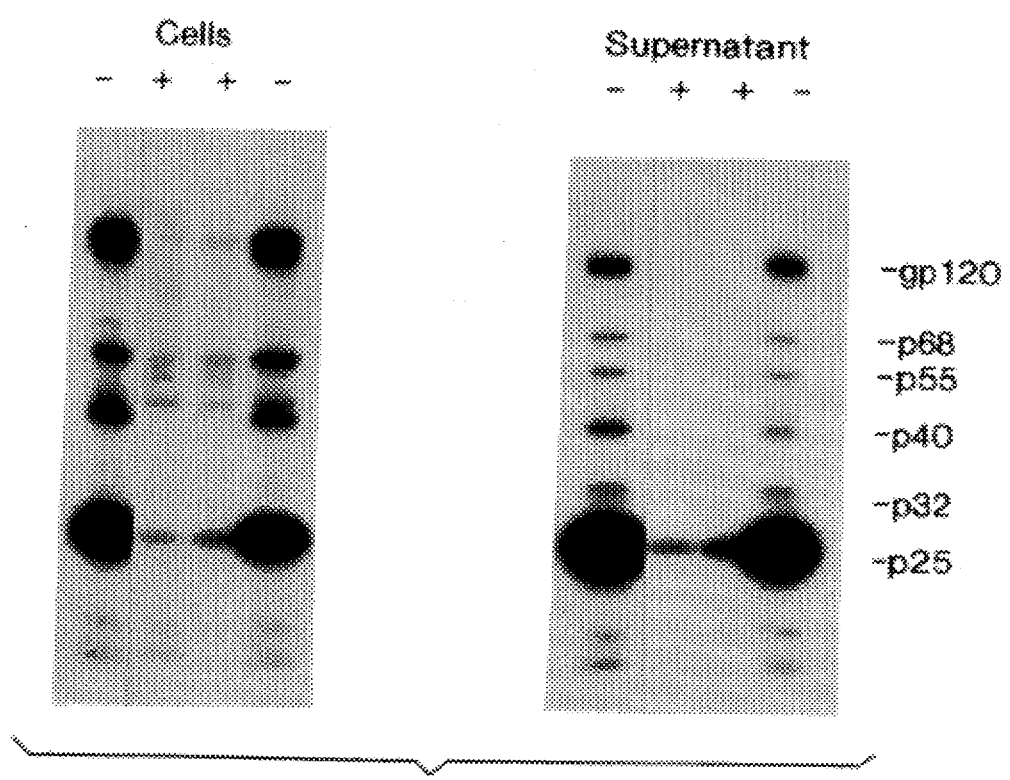

COMPLEXES OF POLYADENYLIC ACID WITH POLYURIDYLIC ACID

PRIOR APPLICATIONS

This application is a division of U.S. patent application Ser. No. 582,658 filed Jan. 4, 1996 which is a continuation of U.S. patent application Ser. No. 437,219 filed May 8, 1995, now abandoned, which is a continuation of U.S. patent application Ser. No. 218,850 filed Mar. 28, 1994, now abandoned, which is a continuation of U.S. patent application Ser. No. 099,048 filed Jul. 28, 1993, now abandoned, which is a continuation of U.S. patent application Ser. No. 866,435 filed Apr. 10, 1992, now abandoned.

The invention relates to pharmaceutical compositions containing complexes of polyadenylic acid with polyuridylic acid (hereinafter referred to as "the complex of Poly(A).Poly(U)" or "PolyA.PolyU"), optionally associated with another anti-AIDS drug, and also to the use of such complexes for the treatment of Acquired Immuno Deficiency Syndrome (AIDS) and related infections.

British Patent No. 2 211 847, which corresponds to U.S. Pat. No. 4,927,755, the relevant teachings of which U.S. patent are incorporated herein by reference, describes a process for the preparation of homopolymers and copolymers of polynucleotides and complexes thereof. Although these products were previously known, previous processes were not able to produce them at an economically acceptable cost without toxic impurities which made them unsuitable for pharmaceutical use. The process described in the aforesaid British patent leads to products of sufficient purity for pharmaceutical use, namely for the treatment of tumors.

The complex of Poly(A).Poly(U) has been described as a poor anti-viral agent (cf "Effects of polynucleotides on monkeys and man", CLINICAL ASPECTS OF INTERFERONS, 1988, pages 319–331). Even though viruses and retroviruses behave somewhat differently, one of skill in the art would not expect that Poly(A).Poly(U) might be an efficient anti-retroviral agent. Contrary to that which would be expected, the applicants have found Poly(A).Poly(U) to be effective in the treatment of AIDS.

It has been found that a complex of Poly(A).Poly(U) is also a potent inhibitory agent of various HIV viruses, by blocking the entry of the virus. The invention thus provides a therapeutic agent for the treatment of AIDS and HIV, wherein the major active ingredient is Poly(A).Poly(U). Preferably, the Poly(A).Poly(U) is prepared by the process described in said British Patent No. 2 211 847.

It has been found that Poly(A).Poly(U) is especially effective when administered with other anti-AIDS drugs, notably 3'-azido-3'-deoxythymidine (AZT), Dideoxyinosine (DDI) or Dideoxycytidine (DDC). Of particular interest is that fact that the complex of Poly(A).Poly(U) has been found to synergistically enhance the effect of AZT, DDI and DDC. Accordingly, a further aspect of the invention is directed to a pharmaceutical composition comprising pharmaceutically acceptable diluents or carriers and a combination of Poly(A).Poly(U) and another anti-AIDS drug acting according to a different mechanism from that of complex of Poly(A).Poly(U), the amount of each component of the combination being selected so that the combination is effective in the treatment of AIDS and/or in the inhibition of HIV.

The invention also provides a method for the treatment of AIDS, the method comprising administering an effective amount of Poly(A).Poly(U), alone or in combination with another anti-AIDS agent, to a patient suffering from AIDS.

Accordingly, this invention provides a therapeutic composition for the treatment of Acquired Immuno Deficiency Syndrome (AIDS) and related infections, said composition comprising as an active ingredient from about 0.1 to 100% of a complex of Poly(A).Poly(U), optionally associated with another anti-AIDS agent acting on HIV viruses according to a different mechanism from that of the complex of Poly(A).Poly(U), and pharmaceutically acceptable diluents or carriers.

According to a preferred embodiment of the invention, the anti-AIDS coagent acting on the HIV virus is selected from the group consisting of AZT, DDI, DDC and combinations of the foregoing. The weight ratio of Poly(A).Poly(U) to the anti-AIDS coagent is suitably from about $1:10^{-1}$ to about $1:10^{-4}$, but is preferably from about $1:10^{-1}$ to about $1:10^{-2}$.

The interest of Poly(A).Poly(U) in the treatment of AIDS will appear clearly from the various experiments hereafter described.

These and other aspects of the present invention may be more fully understood from the following detailed discussion and the drawing, with the drawing showing the viral proteins synthesized during incubation.

CYTOPATHOLOGY

Two batches of CEM cells (T cells rich in CD4 receptors) were infected with Human Immunodeficiency Virus HIV-1 Bru (LAI) and were treated with Poly(A).Poly(U) 24 hours after infection. Two similar batches of HIV infected CEM cells were used as controls, i.e. they were not treated. The cell cultures were regularly inspected under a microscope to observe the onset of cytopathic effects (fusion of cells and formation of syncitia) resulting from the HIV.

The experimental protocols were as follows: $5 \times 10^6$ CEM cells were incubated with 1 ml of supernatent containing HIV with a reverse transcriptase activity of $1.0 \times 10^6$ cpm. One hour afterwards, the cells were centrifuged and the cellular residue ($0.5 \times 10^6$ cells) was suspended in RMP1 medium containing 10% fetal serum and 2 µg/ml polybrene. Twenty-four hours later, Poly(A).Poly(U) was added at a concentration of 200 µg/ml. The cell cultures were maintained without further addition of Poly(A).Poly(U). The results were as follows:

TABLE 1

|  | Day 6 | Day 7 | Day 8 | Day 11 |
|---|---|---|---|---|
| Controls | ++ | ++++ | ++++ | cells dead |
| Treated Cells | − | + | + | ++ |

The symbol "+" indicates the appearance of cytopathic effects; the number of such symbols used is an approximate quantification. These results show that the cytopathic effects are significantly reduced by the treatment.

Cultures were prepared as above described, and during the night of days 7 and 8 were incubated with $^{35}$S-methionine for electrophoretic analysis on SDS of the viral proteins synthesized, both in the cellular mass and in the supernatent. The results are shown in the accompanying drawing. In the drawing, "−" indicates a sample from an untreated control and "+" a sample from a culture treated with Poly(A).Poly(U). The identifiers on the right of the indicators shown are as follows:

| | |
|---|---|
| gp 120 | the envelope protein |
| p68 | reverse transcriptase |
| p55 | precursor of the core protein |
| p40 | precursor of the core protein, partially cleaved |
| p32 | endonuclease |
| p25 | the major core protein |

The results show an almost total reduction of the presence of viral proteins in the cells and supernatents of the cultures treated with Poly(A).Poly(U).

The quantity of p24/p25 antigen in the supernatent was measured 8 days after infection, by the ELISA test. These results are as follows:

TABLE 2

| Controls | Treated Cells |
|---|---|
| 1.01 µg/ml | 0.03 µg/ml |
| 1.27 µg/ml | 0.07 µg/ml |

This shows suppression of 127 96.5% of the HIV production in the cultures treated by Poly(A).Poly(U).

The action of Poly(A).Poly(U) on the inhibition of the production of HIV has been confined by the following experiments.

1. Effect of Variation of the Dose of Poly(A).Poly(U)

CEM cells were infected with HIV. Twenty-four hours later, different concentrations of Poly(A).Poly(U) were added. The production of the virus in the supernatent of the culture was determined on day 5 after infection, by quantifying the amount of p24/p25 antigen present. Control cells, which had been infected but to which Poly(A).Poly(U) had not been added, had by then ruptured. The obtained results were as follows:

TABLE 3

| Poly(A).Poly(U) (µg/ml) | p24/p25 (µg/ml) |
|---|---|
| 0 | 1.10 |
| 25 | 0.53 |
| 50 | 0.14 |
| 100 | 0.10 |
| 200 | 0.07 |

2. Effect of Repeated Treatment

The operating procedure was similar to that described in experiment 1, but addition of Poly(A).Poly(U) was at a concentration of 200 µg/ml at 24 and 96 hours after infection. An untreated control was also run; as before, the cells in the control had ruptured by day 5.

The concentration (µg/ml) of p24/p25 at the days 4, 5, 6 and 7 after infection was measured in the untreated control and in the cells treated at days 1 and 4. The obtained results were as follows:

TABLE 4

| | p24/p25 (µg/ml) | | | |
|---|---|---|---|---|
| | Day 4 | Day 5 | Day 6 | Day 7 |
| Controls | 0.72 | 1.25 | | |
| Treated cells | 0.05 | 0.10 | 0.20 | 0.26 |

3. The Effect of Poly(A).Poly(U) is at an Early Step in Virus Infection

HIV infected cells were treated with 200 µg/ml of Poly(A).Poly(U) at different times before, during and after infection with HIV. On day 6 after infection, the number of syncitia were counted. On day 7, the level of p25 in the culture medium was assayed:

TABLE 5

| Poly(A).Poly(U) | Syncitia (%) | p25 (ng/ml) |
|---|---|---|
| Control (untreated) Cells treated at: | 90 | 1320 |
| •3 days before | 85 | 1215 |
| •2 days before | 72 | 965 |
| •1 day before | 45 | 280 |
| •1 hour before | <5 | 6 |
| •Together with HIV | <5 | 5 |
| •1 hour after | 10 | 110 |
| •4 hours after | 10 | 120 |

STUDY OF USE OF POLY(A).POLY(U) WITH AZT

Cells were infected with HIV 24 hours before a single treatment with:

(a) Poly(A).Poly(U) alone, at a concentration of 100 µg/ml;

(b) AZT alone, at concentrations of 100, 250, 1,000, 5,000 and 10,000 ng/ml, (5 samples);

(c) a combination of (i) AZT at concentrations of 100, 250, 1,000, 5,000 and 10,000 ng/ml, and (ii) in each instance, Poly(A).Poly(U) at a concentration of 100 µg/ml.

A control (non-treated) was also maintained; the cell culture in the control dies progressively after day 7. So, no figure appears in day 12 and day 14 columns. The levels of antigen p25 in the supernatents were measured at days 7, 12 and 14 after infection. The results, expressed in µg/ml, were as follows:

TABLE 6

| | p25 | | |
|---|---|---|---|
| | Day 7 | Day 12 | Day 14 |
| Control | 1250 | | |
| Poly(A).Poly(U) | 135 | 980 | 1200 |
| AZT 100 | 38 | 380 | 1200 |
| AZT 100 Poly(A).Poly(U) | 16 | 75 | 900 |
| AZT 250 | 18 | 170 | 1200 |
| AZT 250 Poly(A).Poly(U) 100 | 5 | 40 | 840 |
| AZT 1000 | <5 | 52 | 590 |
| AZT 1000 Poly(A).Poly(U) 100 | <5 | 17 | 200 |
| AZT 5000 | <5 | 27 | 275 |
| AZT 5000 Poly(A).Poly(U) 100 | <5 | 10 | 48 |
| AZT 10 000 | <5 | 20 | 220 |
| AZT 10 000 Poly(A).Poly(U) 100 | <5 | 8 | 39 |

These results show that the combination of Poly(A).Poly (U) with AZT is more effective than either alone.

The results show that Poly(A).Poly(U) has an inhibitory effect on HIV. This has been observed in different tests:

A) metabolic synthesis of viral proteins in infected cells

B) activity of reverse transcriptase in the culture medium of infected cells

C) amounts of the major core protein p25 of HIV in the culture medium of infected cells; and D) cell fusion The Inhibitory Action of Poly(A).Poly(U) on Different Types and Isolates of HIV In all of the experiments presented above, the HIV-1 Bru isolate (commonly referred to as HIV-1 LAI) was employed. In order to demonstrate that the inhibitory action of Poly (A).Poly(U) is not restricted to the HIV-1 species used, another species of HIV-1 referred to as ELI (31) and two different HIV-2 species, ROD and EHO, were tested. Poly (A).Poly(U) added 6 hours before infestation of CEM cells with these viruses resulted in more than 90% inhibition of virus production.

In all these tests, Poly(A).Poly(U) at a dosage of 200 μg/ml exercises an inhibitory action which is between about 85 and about 90%. For human beings, an amount per single injection of from about 100 to 4,000 mg is considered suitable; doses of from about 150 to 1,000 mg can be efficiently injected into human beings. It is preferred that treatment be as close as possible to the time of infection; however, treatment before of after infection is also effective. The treatment is suitably repeated at intervals of about 3 to 5 days.

The compounds of the present invention are suitably administered by injection in water solution. The active ingredient is added to the water solution. Poly(A).Poly(U) is suitably added at about 0.2 to about 1.0 g per 100 ml water solution. Coagents, such as AZT, DDI and DDC, can suitably be added. The weight ratio of Poly(A).Poly(U) to the anti-AIDS coagent is suitably from about $1:10^{-1}$ to about $1:10^{-4}$. A preferred water solution for use in the present invention is:

| | |
|---|---|
| $NaH_2PO_4$—$H_2O$ | 0.100 g |
| NaCl | 0.068 g |
| NaOH | to neutralize (pH 7) |
| $H_2O$ | q.v. to 100 ml |

In each 100 ml of water solution there is dissolved:

| | |
|---|---|
| Poly(A).Poly(U) | 0.40 g |
| Mannitol | 1.84 g |
| NaCl | 0.48 g |

If one or more coagents is desired, they are cumulatively added to the water solution, i.e. nothing is removed to account for the addition of the coagent. A suitable amount of a coagent, notably AZT, is from about 0.04 mg to about 4 mg per 100 ml of water solution. For example, 150 mg of Poly(A).Poly(U) associated with 15 mg of AZT, may be administered by injection of 38 ml of a water solution as above described.

It has been demonstrated that the complex of Poly(A) .Poly(U) has a potent anti-retroviral action. However, using Poly(A).Poly(U) in combination with another anti-retroviral agent such as AZT, DDI or DDC gives far better results than use of either alone. An explanation for this may be that Poly(A).Poly(U) works at the level of penetration of the virus into the cell, whereas AZT, DDI and DDC work at the level of intra-cellular transcription. Whether or not this is the correct theory for the manner in which the combination of Poly(A).Poly(U) and another anti-retroviral drug is effective, the fact remains that the combination is superior to the use of either agent alone.

It will be understood that the claims are intended to cover all changes and modifications of the preferred embodiments of the invention herein chosen for the purpose of illustration which do not constitute a departure from the spirit and scope of the invention.

What is claimed is:

1. A therapeutic composition for the treatment of Acquired Immuno Deficiency Syndrome (AIDS), said composition comprising as an active ingredient of a complex of Poly(A).Poly(U) and anti-AIDS coagent which acts on the HIV according to a different mechanism from that of the complex of Poly (A).Poly(U) and pharmaceutically acceptable diluents or carriers.

2. The composition of claim 1 wherein the complex of Poly(A).Poly(U) is present in the amount of from about 100 mg to about 4,000 mg per unitary dose.

3. The composition of claim 1 wherein the complex of Poly(A).Poly(U) is present in the amount of from about 150 mg to about 1,000 mg per unitary dose.

4. The composition of claim 1 wherein the weight ratio of Poly(A).Poly(U) to the anti-AIDS coagent is from about $1:10^{-1}$ to about $1:10^{-4}$.

5. The composition of claim 4 wherein the said ratio is from about $1:10^{-1}$ to about $1:10^{-2}$.

6. A therapeutic composition according to claim 5 wherein the anti-AIDS coagent acting on the HIV according to a mechanism different from that one of the Poly(A).Poly (U) complex is selected from the group consisting of AZT, DDI, DDC and combinations of the foregoing.

7. The composition of claim 6 wherein the complex of Poly(A).Poly(U) is present in the amount of from about 100 mg to about 4,000 mg per unitary dose.

8. The composition of claim 6 wherein the complex of Poly(A).Poly(U) is present in the amount of from about 150 mg to about 1,000 mg per unitary dose.

9. The composition of claim 1 wherein the anti-AIDS coagent is AZT and wherein the weight ratio of Poly(A) .Poly(U) to AZT is from about $1:10^{-1}$ to about $1:10^{-4}$.

10. The composition of claim 9 wherein the said ratio is from about $1:10^{-1}$ to about $1:10^{-2}$.

11. The composition of claim 10 wherein the complex of Poly(A).Poly(U) is present in the amount of from about 100 mg to about 4,000 mg per unitary dose.

12. The composition of claim 10 wherein the complex of Poly(A).Poly(U) is present in the amount of from about 150 mg to about 1,000 mg per unitary dose.

13. The composition of claim 10 wherein an unitary dose contains 150 mg of the complex Poly(A).Poly(U) associated with 15 mg of AZT.

* * * * *